United States Patent
Cho et al.

(10) Patent No.: US 10,172,546 B2
(45) Date of Patent: Jan. 8, 2019

(54) SENSOR, NETWORK SYSTEM AND CONTROLLING METHOD FOR USING THE SAME

(71) Applicant: LG INNOTEK CO., LTD., Seoul (KR)

(72) Inventors: Sung Bae Cho, Seoul (KR); Sang Hun Lee, Seoul (KR); Ju Bong Park, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 209 days.

(21) Appl. No.: 14/442,548

(22) PCT Filed: Nov. 28, 2013

(86) PCT No.: PCT/KR2013/010940
§ 371 (c)(1),
(2) Date: May 13, 2015

(87) PCT Pub. No.: WO2014/084646
PCT Pub. Date: Jun. 5, 2014

(65) Prior Publication Data
US 2016/0277871 A1    Sep. 22, 2016

(30) Foreign Application Priority Data

Nov. 29, 2012  (KR) .......................... 10-2012-0137390
Nov. 30, 2012  (KR) .......................... 10-2012-0138228

(51) Int. Cl.
*A61B 5/00*    (2006.01)
*H04W 4/80*    (2018.01)
(Continued)

(52) U.S. Cl.
CPC ............ *A61B 5/4809* (2013.01); *A61B 5/024* (2013.01); *A61B 5/02055* (2013.01);
(Continued)

(58) Field of Classification Search
CPC . A61B 5/02055; A61B 5/0402; A61B 5/4812; A61B 5/4809; A61B 2560/0242; H04W 4/008; H04L 12/12
See application file for complete search history.

(56) References Cited

U.S. PATENT DOCUMENTS 6,547,728 B1 *  4/2003  Cornuejols ............ G04B 25/04
                                                    600/300
6,807,438 B1 * 10/2004  Brun Del Re ..... A61B 5/04004
                                                    128/902
(Continued)

FOREIGN PATENT DOCUMENTS

CN           102573615 A       7/2012

OTHER PUBLICATIONS

Harland et al. "Electric potential probes—new directions in the remote sensing of the human body." Meas. Sci. Technol. 13 (2002). 163-169.*

(Continued)

*Primary Examiner* — Meredith Weare
(74) *Attorney, Agent, or Firm* — Saliwanchik, Lloyd & Eisenschenk

(57) ABSTRACT

Disclosed are a sensor, which includes a cardiac impulse sensor for sensing a cardiac impulse of a human body spaced apart from the cardiac impulse sensor to generate an output signal, and a wireless processing unit for processing and outputting an operation signal of an electronic device according to an output signal of the cardiac impulse sensor, a network system including the sensor, and a method of controlling an electronic device. The electronic device is effectively controlled.

14 Claims, 5 Drawing Sheets

(51) Int. Cl.
*A61B 5/024* (2006.01)
*H04L 12/12* (2006.01)
*A61B 5/0205* (2006.01)
*A61B 5/0402* (2006.01)

(52) U.S. Cl.
CPC ........ *A61B 5/02444* (2013.01); *A61B 5/0402* (2013.01); *A61B 5/4812* (2013.01); *H04L 12/12* (2013.01); *H04W 4/80* (2018.02); *A61B 5/6891* (2013.01); *A61B 5/6898* (2013.01); *A61B 2560/0242* (2013.01)

(56) References Cited

U.S. PATENT DOCUMENTS

| | | | |
|---|---|---|---|
| 8,274,386 B1 | 9/2012 | Dea et al. | |
| 8,306,265 B2 * | 11/2012 | Fry | A61B 5/0452 348/143 |
| 8,535,222 B2 * | 9/2013 | Ni | A61B 5/0205 600/300 |
| 8,536,505 B2 * | 9/2013 | Page | H05B 37/0218 250/205 |
| 8,781,568 B2 * | 7/2014 | Dugan | A61B 5/0002 600/519 |
| 2005/0075553 A1 * | 4/2005 | Sakai | A61B 5/02438 600/372 |
| 2006/0071798 A1 | 4/2006 | Kiff et al. | |
| 2007/0161873 A1 * | 7/2007 | Ni | A61B 5/0205 600/300 |
| 2008/0027337 A1 | 1/2008 | Dugan et al. | |
| 2008/0157964 A1 | 7/2008 | Eskildsen et al. | |
| 2010/0177968 A1 * | 7/2010 | Fry | A61B 5/0452 382/224 |
| 2011/0251495 A1 * | 10/2011 | Province | A61B 5/01 600/483 |
| 2011/0270446 A1 | 11/2011 | Scharf et al. | |
| 2012/0136218 A1 * | 5/2012 | Lee | G06F 19/3418 600/300 |
| 2012/0139427 A1 * | 6/2012 | Tsai | H05B 33/0854 315/158 |
| 2012/0203117 A1 | 8/2012 | Chen et al. | |
| 2013/0009552 A1 * | 1/2013 | Page | H05B 37/0218 315/152 |

OTHER PUBLICATIONS

International Search Report in International Application No. PCT/KR2013/010940, filed Nov. 28, 2013.

Office Action dated Nov. 3, 2017 in Chinese Application No. 201380061614.4.

* cited by examiner

[Fig. 1]
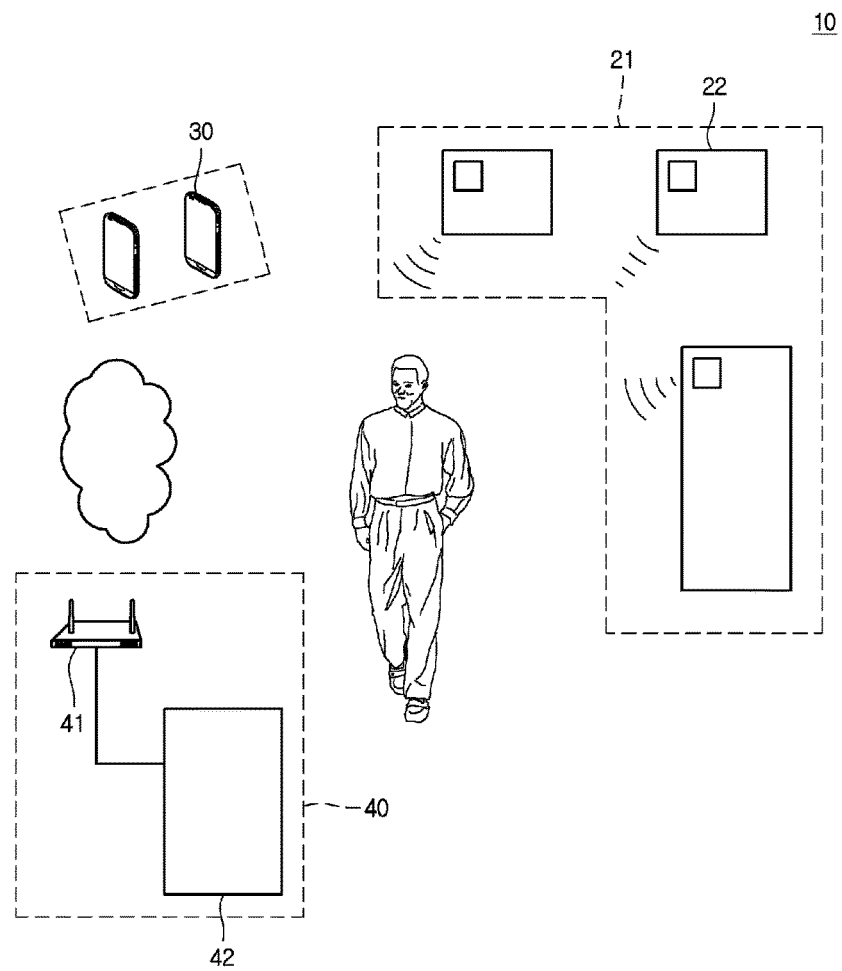
[Fig. 2]
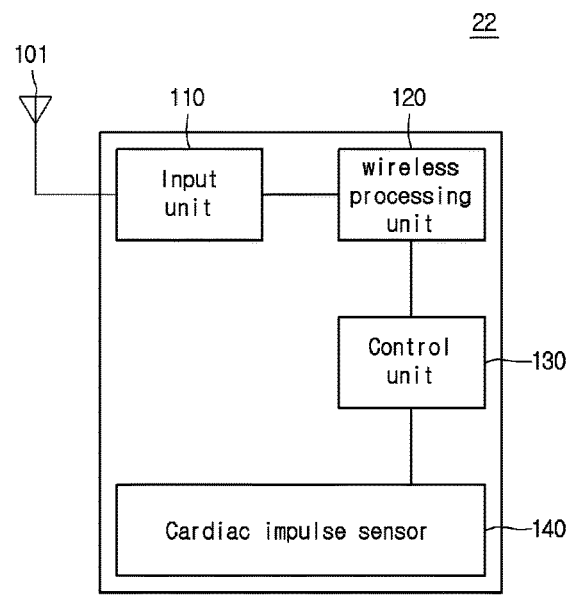

[Fig. 3]
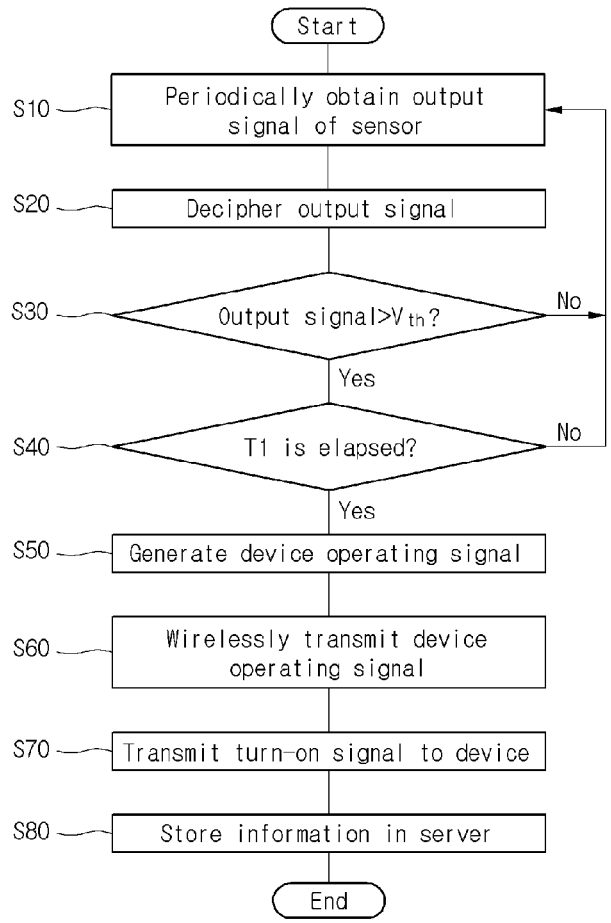
[Fig. 4]
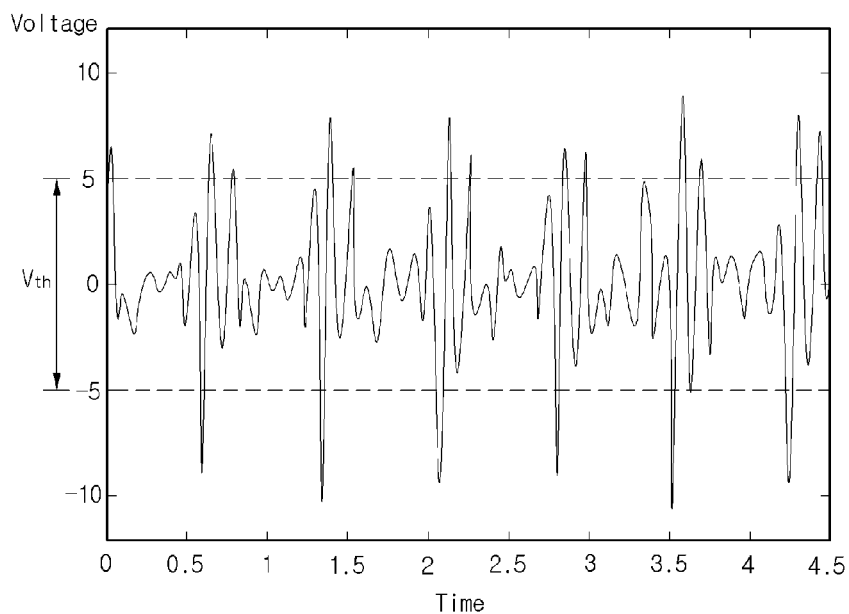

[Fig. 5]
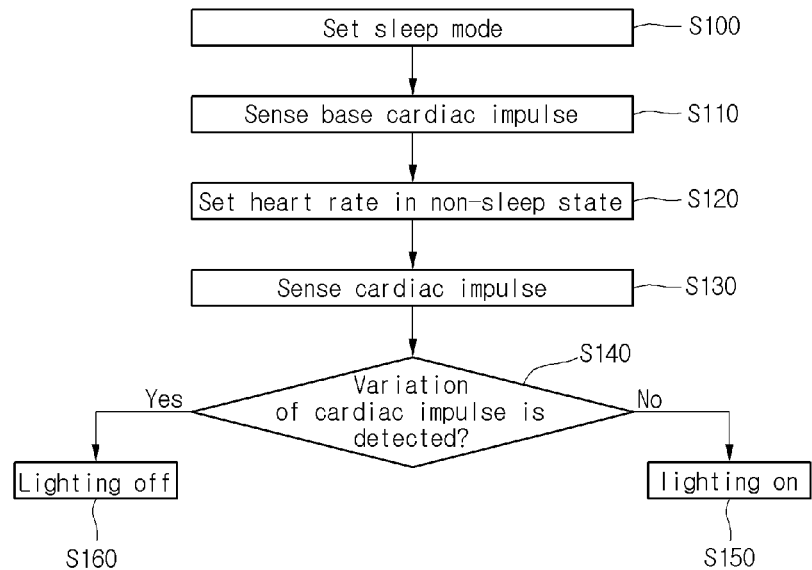
[Fig. 6]
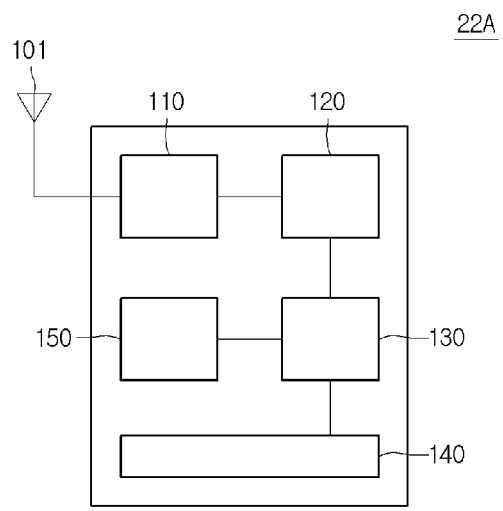

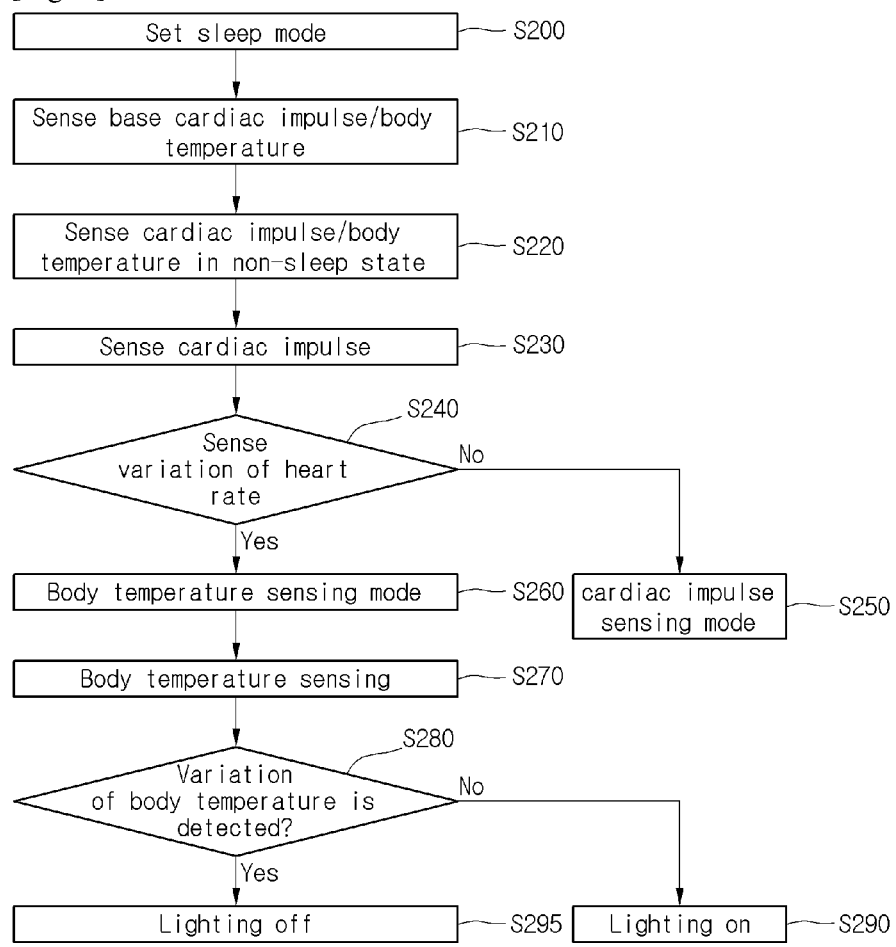
[Fig. 7]

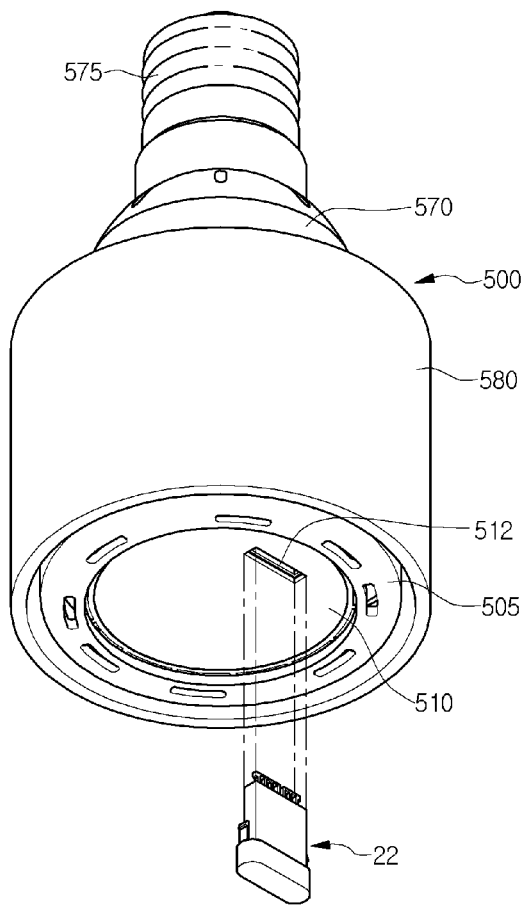
[Fig. 8]

SENSOR, NETWORK SYSTEM AND CONTROLLING METHOD FOR USING THE SAME

CROSS-REFERENCE TO RELATED APPLICATIONS

This application is the U.S. national stage application of international Patent Application No. PCT/KR2013/010940, filed Nov. 28, 2013, which claims priority to Korean Application Nos. 10-2012-0137390, filed Nov. 29, 2012, and 10-2012-0138228, filed Nov. 30, 2012, the disclosures of each of which are incorporated herein by reference in their entirety.

TECHNICAL FIELD

The disclosure relates to a sensor, a network system including the same, and a method of controlling an electronic device using the same.

BACKGROUND ART

In general, home appliances such as home network systems and the like include various sensors.

For example, a conventional pyroelectric infrared ray sensor to mainly sense the presence/absence of a person detects the temperature difference between heat radiated from a moving human body and a background space, so that the absence or the presence of the user can be detected.

However, the pyroelectric infrared ray sensor does not detect the presence state of the person when the person moves at a low speed or stops. In addition the pyroelectric infrared ray sensor may erroneously operate due to the interference resulting from the temperature variation caused by heating/cooling devices such as an indoor air conditioner or a heater.

In addition, the pyroelectric infrared ray sensor cannot sense an optic angle when the optic angle exceeds a predetermined range within the line of sight even if a sensing angle of the pyroelectric infrared ray sensor is increased by using a Fresnel optical lens.

DISCLOSURE OF INVENTION

Technical Problem

The embodiment provides a sensor, a network system including the same, and a method of controlling an electronic device using the same.

Solution to Problem

According to the embodiment, there is provided a sensor including a cardiac impulse sensor for sensing a cardiac impulse of a human body spaced apart from the cardiac impulse sensor to generate an output signal, and a wireless processing unit for processing and outputting an operation signal of an electronic device according to an output signal of the cardiac impulse sensor.

Meanwhile according to the embodiment, there is provided a network system including at least one electronic device, and a sensor module comprising a cardiac impulse sensor for generating an output signal by sensing a cardiac impulse of a human body spaced apart from the sensor module, the sensor module for transmitting an operation signal of the electronic device according to the output signal.

According to the embodiment, there is provided a method of controlling an electronic device. The method includes periodically sensing a cardiac impulse of a human body, generating an operation signal of the electronic device according to the sensed cardiac impulse, and outputting the operation signal.

Advantageous Effects of Invention

As described above, according to the embodiment, since a non-contact cardiac impulse sensor is employed, even if a person stops indoor, the variation in an electric field resulting from the movement of muscles of the person according to the cardiac impulse or the respiration of the person is detected, thereby improving the accuracy of the detection of the presence/absence of the person. In addition, since the electric field can be detected in all directions without an additional lens, the production cost can be improved.

In addition, the home network system according to the embodiment controls the automatic on/off operation according to the presence/absence state of a person, controls the lighting operation according to the illuminance control using the sunlight, and controls an air conditioning operation to reduce the whole load. Accordingly, the total power consumption in a building can be reduced.

Further, a sleep mode is set in the home network system, so that the sleep state/non-sleep state of the person can be determined based on the information from the sensor to control the electronic device.

In addition, the electronic device is formed in a dongle type so that the sensor can be inserted into the communication module through the outer surface of the electronic device. Accordingly, the detachable communication module can be easily coupled with the sensor.

According to the embodiment, the sensor enables the selective implementation of various wireless communication schemes, such as a ZigBee scheme, a Wi-Fi scheme, and a Bluetooth scheme. Accordingly, the optimal wireless communication scheme is selected based on the speed/distance/power consumption, so that the effective data transmission/reception and the effective control can be performed.

BRIEF DESCRIPTION OF DRAWINGS

FIG. 1 is a view showing the structure of a home network system according to one embodiment.

FIG. 2 is a block diagram showing a sensor module of FIG. 1.

FIG. 3 is a flowchart showing the operation of the home network system.

FIG. 4 is a graph showing the waveform of an output signal of the cardiac impulse sensor of FIG. 2.

FIG. 5 is a flowchart showing the operation of the home network system according to a sleep mode.

FIG. 6 is a block diagram showing another application of the sensing module of FIG. 1.

FIG. 7 is a flowchart showing the operation of the home network system employing the sensing module of FIG. 6 according to the sleep mode.

FIG. 8 is a view showing a lighting device as one example of an electronic device in the home network system of FIG. 1.

MODE FOR THE INVENTION

Hereinafter, embodiments will be described in detail with reference to accompanying drawings so that those skilled in the art can easily work with the embodiments. However, the embodiments may not be limited to those described below, but have various modifications. In addition, only components related to the embodiment are shown in drawings for the clarity of explanation. In the following description, the similar reference numerals will be assigned to the similar elements.

In the following description, when a predetermined part "includes" a predetermined component, the predetermined part does not exclude other components, but may further include other components if there is a specific opposite description.

The disclosure provides a home network system to control an electronic device by a sensor.

Hereinafter, a home network system will be described with reference to FIGS. 1 to 4.

FIG. 1 is a view showing the structure of a home network system 10 according to one embodiment. FIG. 2 is a block diagram showing a communication module assembled with a home appliance 21. FIG. 3 is a flowchart showing the operation of the home network system 10. FIG. 4 is a graph showing the waveform of an output signal of the cardiac impulse sensor 140 of FIG. 2.

The home network system 10 includes a home gateway system 40 and a plurality of electronic devices 21.

As shown in drawings, the home gateway system 40 is connected with an external communication network, and connected with a plurality of electronic devices 21 through an internal communication network.

The home gateway system 40 makes an interface for data transceived between an external communication network and the electronic devices 21.

At least one electronic device 21 may be provided. According to the present embodiment, three electronic devices 21 are shown.

In this case, the electronic device 21 may include a portable terminal 30, such as a laptop computer, or a smart phone, connected with the home gateway system 40.

Each electronic device 21 is connected with the home gateway system 40 through a plurality of networks having various shapes.

In this case, the networks having various shapes may transceive data with mutually different transmission bandwidths. The networks may employ wireless schemes such as ZigBee, Bluetooth, Z-wave, or Wi-Fi according to the coverage of the home gateway system 40.

The electronic device 21 not only representatively include a telephone and a computer, but also includes various home appliances, such as an Internet refrigerator, a digital TV, and a set top-box, which are equipped with network functions and may be connected with an external communication network such as a ultra-high speed communication network in home, as various multi-media services are employed.

In addition, the electronic device 21 includes at least one lighting device controlled by a dimming device connected with the home gateway system 40.

Further, the electronic device 21 includes at least one sensing module 22 provided in home. The configuration of the sensing module 22 will be described later.

As shown in FIG. 1, the home gateway system 40 includes a wireless communication unit 41 and a server 42.

The wireless communication unit 41 transmits a turn-on signal to the electronic device 21, which is controlled through a wireless communication scheme in home, through at least one wireless communication scheme.

The server 42 is connected between the wireless communication unit 41 and the external communication network.

The server 42 stores a device operating signal of the electronic device 21 to be transmitted to the wireless communication unit 41, and stores the turn-on signal received from the wireless communication unit 41.

The server 42 may further include a storage unit to store the device operating signal and the turn-on signal.

The server 42 may be connected with a portable terminal 30 through a cloud network serving as an external network to control the electronic device 21 in home.

The electronic device 21 includes at least one sensing module 22 provided in home, and the configuration of the sensing module 22 is shown in FIG. 2.

Referring to FIG. 2, the sensing module 22 includes an input unit 110 connected with an antenna 101, a wireless processing unit 120, a control unit 130, and a cardiac impulse sensor 140.

The antenna 101 transmits the device operating signal to the home gateway system 40 through the wireless network.

The input unit 110 amplifies and filters a signal received therein from the wireless processing unit 120 and transmits the signal to the antenna 101.

The wireless processing unit 120 processes the device operating signal generated from the control unit 130 and generates and outputs a wireless signal having an appropriate frequency.

The control unit 130 obtains an output signal from the cardiac impulse sensor 140, and deciphers the output signal to generate the device operating signal to turn-on a home appliance 21.

The cardiac impulse sensor 140 detects the cardiac impulse of a person spaced apart from the sensor, and may include a potentiometric sensor or an electric field sensor.

In other words, the variation of the fine electric potential difference or the variation of the electric field on a free space according to the cardiac impulse of a human body is detected through a capacitive coupling scheme so that a voltage is output.

In the home network system 10 having the sensing module 22 including a non-contact cardiac impulse sensor 140, the cardiac impulse sensor 140 may generate an output signal according to the absence/presence of a person in home to turn on/turn off the electronic device 21.

Hereinafter, the operation of the home network system 10 of the embodiment will be described with reference to FIGS. 3 and 4.

If the operation of the home network system 10 is started, the cardiac impulse sensor 140 detects the cardiac impulse of a person in a free space (in home according to the embodiment) and generates an output signal related to the cardiac impulse.

The control unit 130 of the sensing module 22 obtains the output signal from the cardiac impulse sensor 140 at a predetermined period (step S10) and determines the absence/presence state of the person.

The output signal of the cardiac impulse sensor 140 is shown in FIG. 4.

In other words, the voltage of a coupled sensing capacitor is varied depending on the variation of the electric field in the free space according to the elapse of time, so that the output voltage is varied.

If a person is present in the free space, so that the potential difference of the free space is greatly made, the output voltage becomes greater than a threshold voltage Vth.

In this case, if the output signal having the threshold voltage Vth or greater is obtained, the person is determined as being present in the free space (step S30).

If the person is determined as being present, the control unit 130 determines if a first reference time T1 elapses after the device operating signal is output (step S40).

If the first reference time T1 elapses, the control unit 130 generates a device operating signal (step S50).

The first reference time T1 may be longer than a period at which the control unit 130 obtains the output signal.

The device operating signal is to turn on the electronic device 21 internetworked in the home network system 10. The electronic device 21 may include a lighting device, an air-conditioner, or a TV.

If the device operating signal is generated, the control unit 130 turns on the wireless processing unit 120, processes the device operating signal as a wireless signal by the wireless processing unit 120, and outputs the wireless signal to the home gateway system 40 through the antenna 101 (step S60).

The home gateway system 40 receives the device operating signal from the sensing module 22 and transmits a turn-on signal to the electronic device 21 through a wireless network (step S70).

In this case, the server 42 stores therein information of the received device operating signal and the output turn-on signal for the electronic device (step S80).

The electronic device 21, which has received the turn-on signal, is turned on according to the turn-on signal. The electronic device 21 keeps on operating during a second reference time T2 even if another turn-on signal is not obtained.

Meanwhile, if the first reference time T1 does not elapse, the sensing module 22 does not generate the device operating signal even if the output signal has the threshold voltage Vth or more.

In other words, an operation according to a previous device operating signal is maintained during the first reference time T1. Accordingly, the power consumption according to the turn-on of the wireless processing unit 120 can be reduced.

The control unit 130 of the sensing module 22 generates the device operating signal according to the output signal having the threshold voltage Vth or more if the first reference time T1 elapses.

The home network system 10 does not transmit the device operating signal to the home gate system 40, but transmits the device operating signal to a dimming device or a switching device internetworking with the home network system 10 through wireless network so that the electronic device 21 may be controlled.

The dimming device or the switching device may record therein the device operating signal and the turn-on signal through a wired/wireless network connected with the home gateway system 40.

The home network system 10 is set to the sleep mode so that the sensing module 22 and the electronic device 21, preferably, a lighting device can be controlled.

Hereinafter, the home network system 10 set to the sleep mode will be described with reference to FIG. 5.

Referring to FIG. 5, a user may set the sleep mode in the home network system 10.

The sleep mode is a mode in which the cardiac impulse of the human body is sensed by using the sensing module 22 to determine if a person is in a sleep state, so that an electronic device 21, preferably, a lighting device is controlled.

If the sleep mode is applied to the home network system 10, the sleep mode is set in the sensing module 22 (step S100).

If the sleep mode is set in the sensing module 22, the sensing module 22 senses a base cardiac impulse (step S110).

The base cardiac impulse is a cardiac impulse within a current sensing range when a human body is in a non-sleep state.

If the sensing of the base cardiac impulse has been finished, the data of the base cardiac impulse are stored in the control unit 130 of the sensing module 22, and the base cardiac impulse is stored in the home gateway system 40.

The sensing module 22 sets the stored base cardiac impulses to a heart rate in a non-sleep sleep and defines the base cardiac impulses as a threshold value used to determine the sleep state/non-sleep state of the human body.

Next, the sensing module 22 senses the cardiac impulses of a human body at a predetermined time as shown in FIG. 3 (step S130).

The sensing scheme of the sensing module 22 is the same as that described with reference to FIG. 3.

In this case, if the sleep mode is set, the threshold value of FIG. 3 becomes the threshold value of the base cardiac impulse, and determination is made regarding if the voltage value of the sensed cardiac impulse is different from the threshold voltage (step S140).

If the voltage value of the sensed cardiac impulse is not different from the threshold voltage, or if the difference between the voltage value of the sensed cardiac impulse and the threshold voltage is within an error margin, the sensing module 22 determines a present state as a non-sleep state and generates a device operating signal to turn on the electronic device 21, preferably, the lighting device (step S150).

Meanwhile, if the difference between the voltage value of the sensed cardiac impulse and the threshold voltage is beyond the error margin, the present state is determined as being a sleep state to generate a device turn-off signal to turn off the lighting device.

The device turn-off/on signal may be directly transmitted to the lighting device from the sensing module 22 according to the home network system 10, or may directly control the lighting device while control information is being transmitted to the gateway system 40 and recorded.

On the contrary, as shown in FIG. 3, the device turn-off signal is transmitted to the home gateway system 40, and the home gateway system 40 may transmit the device turn-off signal to the lighting device.

The home network system 10 having the sensing module 22 including the cardiac impulse sensor 140 sets a present mode to a sleep mode to control the lighting device according to the sleep state/the non-sleep state of the person.

Hereinafter, another embodiment will be described with reference to FIG. 6.

Referring to FIG. 6, the sensing module 22 includes the input unit 110 connected with the antenna 101, the wireless processing unit 120, the control unit 130, the cardiac impulse sensor 140, and an auxiliary sensor 150.

The antenna 101 transmits the device operating signal to the home gateway system 40 through a wireless network.

A wireless communication unit 430 processes the device operating signal generated from the control unit 130 and produces and outputs a wireless signal having an appropriate frequency.

The control unit 130 obtains an output signal from the cardiac impulse sensor 140, and deciphers the output signal to produce the device operating signal to turn-on the home appliance 21.

The cardiac impulse sensor 140 detects the cardiac impulse of a person spaced apart from the sensor, and may include a potentiometric sensor or an electric field sensor.

The home network system 10 having the sensing module 22 including a non-contact cardiac impulse sensor 140 may produce output signals according to the absence/presence of a person in home to turn on/turn off the electronic device 21.

The auxiliary sensor 150 may include an illuminance sensor or a temperature sensor.

The illuminance sensor may read the current variation of the sunlight in home in real time and transmit a value measured as interior illuminance to the control unit 130.

The control unit 130 may generate a device operating signal, that is, an on/off signal of a lighting module 500 by combining output signals of the cardiac impulse sensor 140 and the illuminance sensor.

If the illuminance sensor is provided and if an amount of the sunlight represents a threshold or more even if the person is present indoor, the device operating signal for the lighting module 500 may not be generated.

The temperature sensor reads the variation of the interior temperature in real time and transmits the variation of the interior temperature to the control unit 130.

The control unit 130 may generate a device operating signal, that is, an on/off signal of a lighting device, an air-conditioner, or a boiler by combining the output signals of the cardiac impulse sensor 140 and the temperature sensor.

If the temperature sensor is provided and if a temperature is within a threshold value range even if a person is present indoor, the device operating signal for a temperature adjusting device may not be generated.

Hereinafter, the sleep mode of a home network system including a sensing module 22 of FIG. 6 will be described with reference to FIG. 7, Referring to FIG. 7, a user may set a sleep mode in the home network system 10.

The sleep mode is a mode in which cardiac impulse and temperature variation of the human body are sensed by using the sensing module 22 to determine if a person is in a sleep state, so that an electronic device 21, preferably, a lighting device is controlled.

If the sleep mode is applied to the home network system 10, the sleep mode is set in the sensing module 22 (step S200).

If the sleep mode is set in the sensing module 22, the sensing module 22 senses a base cardiac impulse and a base body temperature (step S210).

The base cardiac impulse is a cardiac impulse within a current sensing range when a human body is in a non-sleep state.

The base temperature refers to a temperature of a human body within a current sensing range when the human body is in the non-sleep state.

If the base cardiac impulse and the base body temperature are sensed completely, the base cardiac impulse and the base body temperature data are stored in the control unit 130 of the sensing module 22. The base cardiac impulse and the base body temperature are stored in the home gateway system 40.

The sensing module 22 sets the base cardiac impulse and the base body temperature to a heart rate and a body temperature in the non-sleep state, respectively, to define the cardiac impulse and the body temperature in the non-sleep state as threshold values for the determination of the sleep state/the non-sleep state of the human body (step S220).

Next, the sensing module 22 periodically senses the cardiac impulse of the human body as shown in FIG. 3 (step S230).

The sensing scheme of the sensing module 22 is the same as that described with reference to FIG. 3.

In this case, if a present mode is set as the sleep mode, the threshold voltage of FIG. 3 becomes a threshold value of the base cardiac impulse, and determination is made regarding if the sensed voltage value of the cardiac impulse is different from the threshold voltage (step S240).

If the difference between the sensed voltage value and the threshold voltage is not made, or is within an error margin, the electronic device 21, preferably, the lighting device is maintained in the turn-on state, so that the sensing of the cardiac impulse is periodically performed (step S250).

On the contrary, if the difference between the sensed voltage value and the threshold value is beyond the error margin, the sensing module 22 senses the temperature (step S260).

If the difference between the temperature and the threshold value is not made, or the difference between the temperature and the threshold value is within the error margin, the electronic device 21, preferably, the lighting device is maintained in the turn-on state (step S290).

On the contrary, if the difference between the temperature value and the threshold value exceeds the error margin, the person is determined as being in the sleep state, so that the device turn-off signal to turn off the lighting device is transmitted (step S295).

The device turn-off/on signal may be directly transmitted to the lighting device from the sensing module 22 according to the home network system 10, or may directly control the lighting device while control information is being transmitted to the gateway system 40 and recorded.

On the contrary, as shown in FIG. 3, the device turn-off signal is transmitted to the home gateway system 40, and the home gateway system 40 may transmit the device turn-off signal to the lighting device.

As described above, two sensing operations are performed through the cardiac impulse sensor 140 and the temperature sensor, so that accurate data can be found. In addition, the sleep mode is set, so that the lighting device can be controlled according to the sleep state and the non-sleep state of a person.

Meanwhile, the sensing module 22 may be provided separately from the electronic device 21 controlled according to the device operating signal as shown in FIG. 1, or may be attached to the electronic device 21.

Referring to FIG. 8, an electronic device 21A includes the sensing module 22 of FIG. 2. For example, the electronic device 21A includes a lighting device.

In other words, if the electronic device 21A is a lighting device, a wireless communication module is required to make communication through the home gateway system 40 and a wireless network.

The electronic device 21A of FIG. 6 serves as the wireless communication module and includes the sensing module 22.

If the sensing module 22 is attached to the electronic device 21A, the control unit 130 of the sensing module 22 receives output signals from the cardiac impulse sensor 140 and the auxiliary sensor 150 to generate a device operating signal, and the wireless processing unit 120 processes and outputs the device operating signal.

In this case, if the home gateway system 40 generates and outputs the turn-on signal according to the device operating signal, the sensing module 22 receives the turn-on signal and transmits the turn-on signal to the control unit 130 of the connected electronic device 21.

Accordingly, the electronic device 21 can receive the control signal by using the wireless processing unit 120 of the sensing module 22 without an additional wireless communication module, so that the cost can be reduced.

The sensing module 22 serving as a communication module constituting the lighting device is a detachable sensing module that is fixedly inserted into an insertion groove 511 of a lighting module 500 to transmit a control signal.

The lighting device includes an insertion groove in which a plurality of pins provided in an interface unit of the sensing module 22 are fixedly inserted.

As shown in FIG. 8, the insertion groove 511 may be exposed to the surface, and may be connected with the control unit 130 including a power supply unit of the lighting module 500.

Since the sensing module 22 constituting the communication module of the lighting device is detachably assembled with the lighting module 500 as described above, the communication module can be reused when a lighting unit (not shown) or a power supply unit of the lighting module 500 is replaced with new one.

The sensing module 22 may constitute one housing, or may constitute one unit provided in the housing.

Meanwhile, the lighting module 500 includes a connector 575 provided at the upper portion thereof, and includes an inner case 570 provided in the lower portion thereof with an insertion part, a heat radiation body (not shown), into which an insertion part of the inner case 570 is inserted, a light emitting module unit to radiate heat downward of the heat radiation body and including a plurality of light emitting devices, a guide member 505 coupled with a lower peripheral portion of the heat radiation body and securely fixed to the heat radiation body of the light emitting module unit, a lens 510 between the guide member 505 and the light emitting module unit, and an external case 580 provided outside the heat radiation body.

The lens 510 includes a lens opening 512 into which a communication module 400 is inserted, and the sensing module 22 inserted through the lens opening 512 is connected with a connector of the power supply unit to transmit an output signal according to the control signal transmitted through the wireless network to the lighting module 500.

Although embodiments have been described in detail, the scope of the disclosure is not limited thereto, but various variations and modifications made by those skilled in the art based on the basic concept of the disclosure defined in claims belong to the scope of the disclosure.

The invention claimed is:

1. A sensing device comprising:
a cardiac impulse sensor for sensing a cardiac impulse of a human body physically spaced apart from the cardiac impulse sensor to generate an output signal;
a control unit for periodically receiving the output signal of the cardiac impulse sensor, comparing the output signal with a threshold value, and generating a first operation signal of an electronic device, and transmitting the first operation signal to a processing unit; and
the processing unit for processing and outputting the first operation signal to the electronic device according to the output signal of the cardiac impulse sensor,
wherein the sensing device is configured to be capable of operating in a sleep mode where:

if the sleep mode is set in the cardiac impulse sensor, the cardiac impulse sensor senses a base cardiac impulse;
the base cardiac impulse is a cardiac impulse of the human body existing within a present sensing range of the cardiac impulse sensor at a time when the sleep mode is set;
the control unit stores the output signal corresponding to the base cardiac impulse, sets the stored base cardiac impulse to a heart rate in a non-sleep state, and defines the base cardiac impulse as the threshold value used to determine a sleep state or a non-sleep state of the human body;
the cardiac impulse sensor continues to sense a continuing cardiac impulse of the human body; and
the control unit periodically compares the output signal corresponding to the continuing cardiac impulses to the threshold value and determines whether a difference between the output signal corresponding to the continuing cardiac impulse and the threshold value is within or greater than an error margin, determines whether a first reference time has elapsed after determination that the difference between the output signal corresponding to the continuing cardiac impulse and the threshold value is greater than the error margin, and generates the first operation signal if both the first reference time has elapsed and the difference between the output signal corresponding to the continuing cardiac impulse and the threshold value is greater than the error margin;
wherein the control unit does not generate the first operation signal in the event that the first reference time does not elapse or the difference is within the error margin,
wherein the control unit turns the processing unit on when the first operation signal is generated,
wherein the cardiac impulse sensor is configured to be inserted into the electronic device,
wherein the first operation signal directly controls the electronic device, and
wherein control information of the first operation signal to the electronic device is wirelessly transmitted to a home gateway system and recorded.

2. The sensing device of claim 1, wherein the cardiac impulse sensor generates the output signal by sensing variation of an electric field in a free space according to the cardiac impulse of the human body.

3. The sensing device of claim 1, further comprising an auxiliary sensor,
wherein the control unit generates the first operation signal by combining the output signal of the cardiac impulse sensor with an output signal of the auxiliary sensor.

4. The sensor of claim 3, wherein the auxiliary sensor includes an illuminance sensor that reads a present variation of sunlight in real time.

5. The sensor of claim 3, wherein the auxiliary sensor includes a temperature sensor that reads a variation of temperature in real time.

6. A network system, comprising:
the sensing device of claim 1;
the electronic device, operation of which is managed by the first operation signal of the sensing device; and
the home gateway system comprising a wireless communication unit for wirelessly communicating with the processing unit, and a server.

7. The network system of claim 6, wherein the home gateway system communicates with the electronic device and the processing unit through a wireless network, and the wireless network is formed through at least one of a ZigBee scheme, a Bluetooth scheme, a Z-wave scheme, and a Wi-Fi scheme.

8. The network system of claim 6, wherein the electronic device is formed in a dongle type such that the sensing device is inserted thereinto.

9. The network system of claim 6, wherein the sensing device includes an auxiliary sensor, the control unit generating the first operation signal based on the output signal from the cardiac impulse sensor and an output signal from the auxiliary sensor.

10. The network system of claim 9, wherein the auxiliary sensor includes an illuminance sensor that reads a present variation of sunlight in real time.

11. The network system of claim 9, wherein the auxiliary sensor includes a temperature sensor that reads a variation of temperature in real time.

12. A method of controlling an electronic device, the method comprising:
sensing a base cardiac impulse of a human body when a sleep mode is set in a cardiac impulse sensor, wherein the base cardiac impulse is a cardiac impulse of the human body existing within a present sensing range of the cardiac impulse sensor at a time when the sleep mode is set;
storing an output signal corresponding to the base cardiac impulse as a threshold value to establish a non-sleep state heart rate;
periodically sensing a continuing cardiac impulse of the human body within the present sensing range after the threshold value is stored;
comparing an output signal corresponding to the continuing cardiac impulse to the threshold value;
determining whether a difference between the output signal corresponding to the continuing cardiac impulse and the threshold value is within or greater than an error margin;
determining whether a first reference time elapses upon determination that the difference between the output signal corresponding to the continuing cardiac impulse and the threshold value is greater than the error margin; and
generating an operation signal if both the first reference time has elapsed and the difference between the output signal corresponding to the continuing cardiac impulse and the threshold value is greater than the error margin,
wherein the operation signal is not generated when the first reference time does not elapse or the difference between the output signal corresponding to the continuing cardiac impulse and the threshold value is within the error margin,
wherein the operation signal directly controls the electronic device, and
wherein control information of the operation signal to the electronic device is wirelessly transmitted to a home gateway system and recorded.

13. The method of claim 12, wherein the generating of the operation signal comprises:
generating the operation signal configured to power the electronic device off.

14. The method of claim 13, wherein the generating of the operation signal comprises:
sensing a temperature of the human body if the difference between the output signal corresponding to the continuing cardiac impulse and the threshold value is greater than the error margin;
determining a sleep state of the human body according to the sensed temperature of the human body; and
generating the operation signal according to the sleep state of the human body.

* * * * *